United States Patent [19]

Green et al.

[11] Patent Number: 4,876,205

[45] Date of Patent: Oct. 24, 1989

[54] ELECTROCHEMICAL ASSAY FOR HAEMOGLOBIN

[75] Inventors: Monika J. Green, Buckinghamshire; Roger J. Lias, Oxon, both of Great Britain

[73] Assignee: Medisense, Inc., Cambridge, Mass.

[21] Appl. No.: 84,983

[22] Filed: Aug. 12, 1987

[30] Foreign Application Priority Data

Aug. 12, 1986 [GB] United Kingdom ................ 8619627

[51] Int. Cl.$^4$ ...................... G01N 27/56; G01N 33/49
[52] U.S. Cl. .......................................... 436/66; 422/98
[58] Field of Search ...................... 436/66; 356/40–42; 128/637

[56] References Cited

U.S. PATENT DOCUMENTS

| | | | |
|---|---|---|---|
| 3,374,063 | 3/1968 | Nöller | 436/66 |
| 3,921,066 | 11/1975 | Angel et al. | 356/40 |
| 4,225,410 | 9/1980 | Pace | 422/98 |
| 4,321,577 | 3/1982 | Carlson | 422/98 |
| 4,350,660 | 9/1982 | Robinson et al. | 422/98 |
| 4,675,310 | 6/1987 | Chapman et al. | 514/76 |

OTHER PUBLICATIONS

Schenck et al., "Evaluation of 'HemoCue', a New Device For Determining Hemoglobin", Clinical Chem. 32/3, 526–529 (1986).

Kobos et al., Clin. Chem. 33(1):153 et seq. (1987).

Primary Examiner—Barry S. Richman
Assistant Examiner—Timothy M. McMahon

[57] ABSTRACT

A method for the assay of haemoglobin in blood is provided in which the blood is contacted with a sufficient amount of a ferricyanide and the haemoglobin is electrochemically assayed by monitoring the current changes produced on reduction of the ferricyanide by the haemoglobin.

8 Claims, 3 Drawing Sheets

ELECTROCHEMICAL ASSAY FOR HAEMOGLOBIN

This invention relates to an electrochemical assay for haemoglobin.

The level of haemoglobin in blood is routinely measured in clinical laboratories. A number of clinical conditions cause changes in haemoglobin levels, such as severe dehydration, primary and secondary polycythemia, and congestive heart failure (all of which lead to increased levels), together with various anaemias (decreased levels). Additionally, some drugs produce decreased haemoglobin concentrations in whole blood, as described by Young et al. in Clin Chem (1975) 21 1D.

There are a number of well known techniques for assaying haemoglobin concentration. It is however important that such techniques should have a reasonable degree of accuracy, since haemoglobin content even in healthy individuals can vary with age, sex, and race. Normal levels are given in the following table.

|  | [Haemoglobin] |
|---|---|
| Adult men | 15.5 ± 2.5 g/dl |
| Adult women | 14.0 ± 2.5 g/dl |
| Infants (full term, cord blood) | 16.5 ± 3.0 g/dl |
| Children, 3 months | 11.0 ± 1.5 g/dl |
| Children, 1 yr | 12.0 ± 1.0 g/dl |
| Children, 3–6 yrs | 13.0 ± 1.0 g/dl |
| Children, 10–12 yrs | 13.0 ± 1.5 g/dl |

Haemoglobin levels are also affected by posture, altitude, exercise and possibly diurnal variations. A change of posture from upright to recumbent position produces around a 5% decrease in sample haemoglobin concentrations over a 20 minute period. Moreover, regular muscular activity can increase haemoglobin levels by up to 1.5 g/dl, and haemoglobin concentration is about 1 g/dl higher at 6500 ft and 2 g/dl higher at 10000 ft, compared to a reading taken at sea level.

Known methods of assay which are accurate enough to give meaningful results have regard to these differences between subjects, behaviour and location, are generally based upon colorimetric examination, as recommended by the International Committee for Standardisation in Haemotology (see, for example, British Journal of Haemotology 13 (Supplement) 68–75 or American Journal of Clinical Pathology 47 212 (1967)).

The most widely used assay method in the colorimetric field is the determination of cyanomethaemoglobin using whole blood as starting material. This technique is based upon the work of Stadie, J. Biol Chem (1920) 41 237 and involves the oxidation of haemoglobin to methaemoglobin with ferricyanide. The methaemoglobin is then stabilised by reaction with potassium cyanide to form a cyanomethaemoglobin derivative which is then detected photometrically by the measurement of absorbance at 540nm. The reaction is as follows:

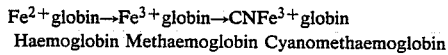

$Fe^{2+}$ globin → $Fe^{3+}$ globin → $CNFe^{3+}$ globin
Haemoglobin  Methaemoglobin  Cyanomethaemoglobin This method has been modified by the use of Drabkin's reagent (see, for example, Drabkin et al. J.Biol Chem (1932) 98 719) which comprises an alkaline aqueous solution of potassium ferricyanide and potassium cyanide and thus allows the assay to be performed using a single reagent. Further modifications include the proposal by Vanzetti in J. Lab. Clin. Med. (1966) 67 116 using sodium azide in place of potassium cyanide. The azide-methaemoglobin has a similar absorption spectrum to that of cyanomethaemoglobin.

In the above methods, lyophilised human methaemoglobin reconstituted in Drabkins reagent can be utilised as a standard and is stable for 6 months when refrigerated.

The disadvantages of the above photometric assay of haemoglobin are the high dilution of the blood sample in the Drabkin's reagent (usually 1:250) leading to inherent inaccuracies in the test, especially when performed by untrained personnel; and turbidity of samples caused by the presence of proteins, cell stromata, lipid particles and the like in the sample which can lead to erroneously high results. The assay is also relatively slow, and requires an incubation step of at least 15 minutes at room temperature, or even more if the specimen contains high levels of carboxyhaemoglobin, for example in blood obtained from heavy smokers.

Another known method, which overcomes some of the above disadvantages, is available under the Trade Mark "HemoCue" from Aktiebolaget Leo Diagnostics, Sweden. This method utilises small plastic cuvettes in which dry assay reagents are deposited. Whole blood is drawn into the cuvette by capillary action. The red cells in the blood are lysed within the cuvette by sodium deoxycholate. Sodium nitrite is then used to convert the haem iron from the ferrous form to the ferric form to produce methaemoglobin, which is stabilised by reaction with sodium azide to form azide-methaemoglobin. The absorbance is measured at 565 nm and 880 nm to allow correction for background turbidity. However, the system is not fully accurate and in particular the entrapment of small air bubbles in the microcuvettes can produce erroneous absorbance measurements.

The present invention sets out to improve upon the above photometric techniques by the use of direct electrochemical measurement of the current changes produced upon reduction of ferricyanide with haemoglobin.

In one aspect the invention consists of a method for the assay of haemoglobin in blood in which the blood is contacted with a sufficient amount of a ferricyanide (preferably potassium ferricyanide) and the haemoglobin is electrochemically assayed by monitoring the current changes produced on reduction of the ferricyanide by the haemoglobin.

The invention is based upon the reversible electrochemistry of the ferricyanide/ferrocyanide couple in accordance with the following scheme.

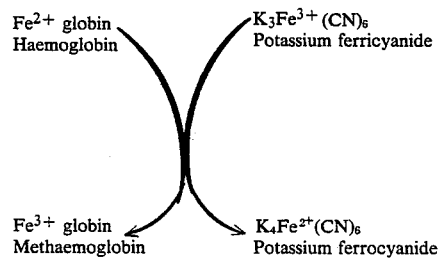

$Fe^{2+}$ globin          $K_3Fe^{3+}(CN)_6$
Haemoglobin              Potassium ferricyanide $Fe^{3+}$ globin          $K_4Fe^{2+}(CN)_6$
Methaemoglobin           Potassium ferrocyanide The assay method is suited for use with various blood samples, including whole blood and blood haemolysate samples. Where the blood has not already been lysed to release the haemoglobin, the blood sample will need to be subjected to lysis, for example by treatment before or as part of the assay with a haemolytic agent such as ethylenediamine tetra-acetic acid (EDTA), saponin, sodium deoxycholate, an ionic detergent, or a non-ionic detergent.

The amount of ferricyanide contacted with the blood sample will typically be in the range 50 to 100 mg per ml of blood (calculated as ml of whole blood).

The current changes are monitored at a fixed potential, preferably by measuring the current time (i-t) transient at a suitable potential against a reference electrode. A suitable potential will be in the general range from 400 to 500 millivolts against a standard calomel electrode, SCE.

The electrode used for measurement can be of conventional electrode material, and preferably a type of carbon, for example a glassy carbon or pyrolytic graphite.

In an alternative embodiment method of this invention, the electrode is itself coated with a dry mixture containing finely divided ferricyanide, preferably potassium ferricyanide, together with a surfactant to facilitate dissolution of the ferricyanide into a blood sample applied thereto, and optionally also with a buffering agent.

The above mixture can further comprise ultrafine carbon and/or finely divided silica, respectively to improve the electrical or physical properties of the mix. Typically such a mixture is applied to form an electrode on a conductive track of a support, for example in the close proximity of a reference electrode mixture connected to a second track, whereby a miniaturised sensor capable of operating upon a small sample of blood bridging the electrode areas may be produced. The mixture is suitably applied by screen printing. Where the sensor is to be used with whole blood or other unlysed blood samples, the sensor preferably incorporates a haemolytic agent, either in the applied mixture or elsewhere, for example as a coating on a mesh overlaying the applied mixture.

In a particularly preferred embodiment, the present invention provides a dry strip sensor which comprises an elongate, electrically-insulating substrate having a pair of longitudinal, substantially parallel, electrically-conducting tracks thereupon, each track being provided at the same end with means for electrical connection to a read-out means and provided at the other end with an electrode, one of the electrodes being the reference electrode and the other being the working electrode formed from a reagent mix of at least the ferricyanide, surfactant, and optional buffering agent.

More especially, such a sensor is suitably configured in the form of a supporting strip of electrically insulating material such as a synthetic polymer (for instance pvc) carrying at a location between its ends the two electrodes supported on electrically conductive printed tracks. For example, the electrodes can take the form of two rectangular areas side by side on the strip, one area comprising the reagent mix and the other area comprising an Ag/AgCl composition as a reference electrode. Such areas can be configured to be covered by a single drop of blood for testing for haemoglobin. If desired, non-rectangular electrode areas, for instance diamond-shaped, semicircular, or triangular areas, can be employed to provide a jointly occupied area for optimised contact by a liquid sample.

The invention will be further described with reference both to the accompanying Examples and the accompanying drawings in which.

EXAMPLE 1

Wet electrochemical assay for haemoglobin in haemolysates

Fresh whole blood was spun at 2000 rpm and the supernatant was discarded. The red cells were resuspended in 5 volumes of Na-phosphate buffer (10 mM; pH 6.8) containing $10^{-4}$M EDTA. The mixture was shaken and then allowed to stand for 15 minutes. Samples at the following dilutions were produced in the same buffer:

| Sample | Haemolysate ($\mu$l) | Buffer ($\mu$l) |
| --- | --- | --- |
| A | 500 | 0 |
| B | 450 | 50 |
| C | 400 | 100 |
| D | 350 | 150 |
| E | 300 | 200 |
| F | 250 | 250 |
| G | 200 | 300 |
| H | 150 | 350 |
| I | 100 | 400 |
| J | 50 | 450 |
| K | 0 | 500 |

50 $\mu$l aliquots of each sample were added to 700 $\mu$l of Tris/HCl buffer (0.1 M; pH 8.5) containing KCl (100 mM), MgCl$_2$ (50 mM) and potassium ferricyanide (20 mM). The mixture was stirred for 50 seconds and allowed to stand for a further 10 seconds. Current-time (i-t) transients at +450 mV versus SCE were then produced using a glassy carbon electrode.

Figure 1:
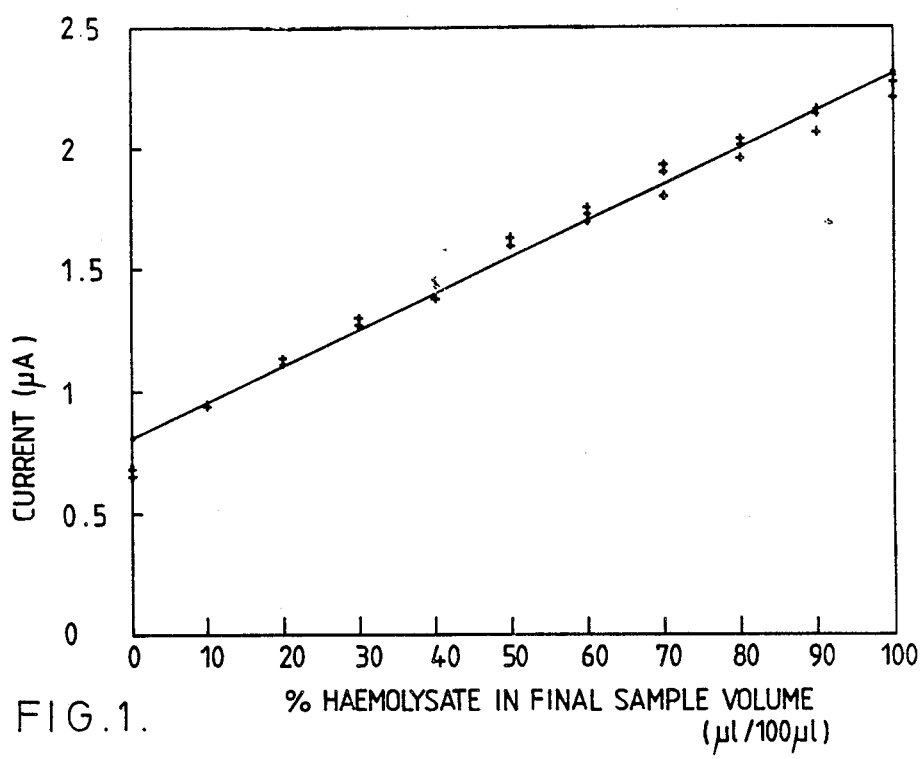
FIG. 1 is a haemoglobin calibration curve obtained in Example 1 using haemolysed samples diluted in buffer, showing current in microamps against haemolysate dilution.

The resultant haemoglobin calibration curve is shown in FIG. 1, and shows an excellent correlation between current and haemoglobin level.

EXAMPLE 2

Wet electrochemical assay for haemoglobin in whole blood

Varying volumes of whole blood were added to 600 $\mu$l aliquots of the ferricyanide mixture used in Example 1 supplemented with 1% (w/v) saponin. The mixture was stirred for 50 seconds and allowed to stand for a further 10 seconds before producing i-t transients at +400 mV versus SCE using a glassy carbon electrode.

The haemoglobin calibration curve produced after correction for dilution effects again showed an excellent correlation between current and haemoglobin level.

EXAMPLE 3

Wet electrochemical assay for haemoglobin in whole blood diluted in serum

To 100 μl aliquots of the ferricyanide mixture used in Example 2 were added 50 μl samples of freshly collected whole human blood and samples diluted in serum from the same source. The mixture was stirred for 50 seconds and allowed to stand for a further 10 seconds before producing i-t transients at +400 mV versus SCE with a glassy carbon electrode. The electrode was polished with alumina/water paste and sonicated between each sample assay. A calibration curve was produced by plotting currents measured at 30 seconds against haemoglobin concentration as determined by a standard photometric assay using Drabkin's reagent (Sigma Diagnostics). A good correlation was obtained up to about 12 g/dl haemoglobin. The saturation and reduced reproducibility at higher haemoglobin concentrations were probably due to matrix effects (high viscosity and higher diffusional restraints).

EXAMPLE 4

A dry strip assay for total haemoglobin in whole blood
Ball-milled potassium ferricyanide was made into a working electrode mix comprising the following:

| | |
|---|---|
| 5.0 ml | Tris/HCl buffer (0.1 M, pH 8.5) |
| 2% (w/w) | Polyvinyl alcohol |
| 0.1 M | KCl |
| 17.0 g | Ball-milled potassium ferricyanide |
| 1% (w/v) | Saponin |
| 250 μl | Print aid, Clerol (Trade Mark for a mix of Polyethylene oxide, polypropylene oxide and emulsifiers) |

The mix was localised as an electrode area in electrical connection with the main electrode system.

In this mix, carbon has been excluded, allowing the electrochemistry to take place on the parent carbon electrode. Other working electrode formulations can be adopted, for example using ferricyanide/ultra-fine carbon and ferricyanide/silica mixtures in place of the ball-milled ferricyanide.

A calibration curve for total haemoglobin in whole blood was produced using the working mix and the following assay protocol.

Figure 2:
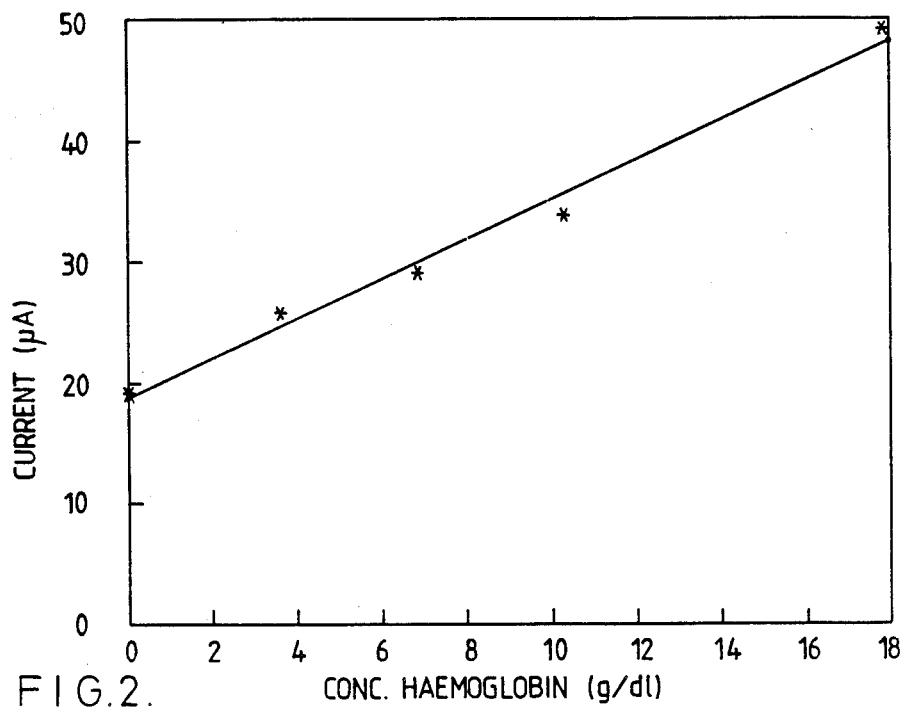
FIGS. 2 and 3 are calibration curves obtained in Example 4 respectively on whole blood samples and on whole blood diluted in serum utilising a dry strip sensor, the measurements being on haemoglobin in g/dl as measured by a standard colorimetric technique.
Figure 3:
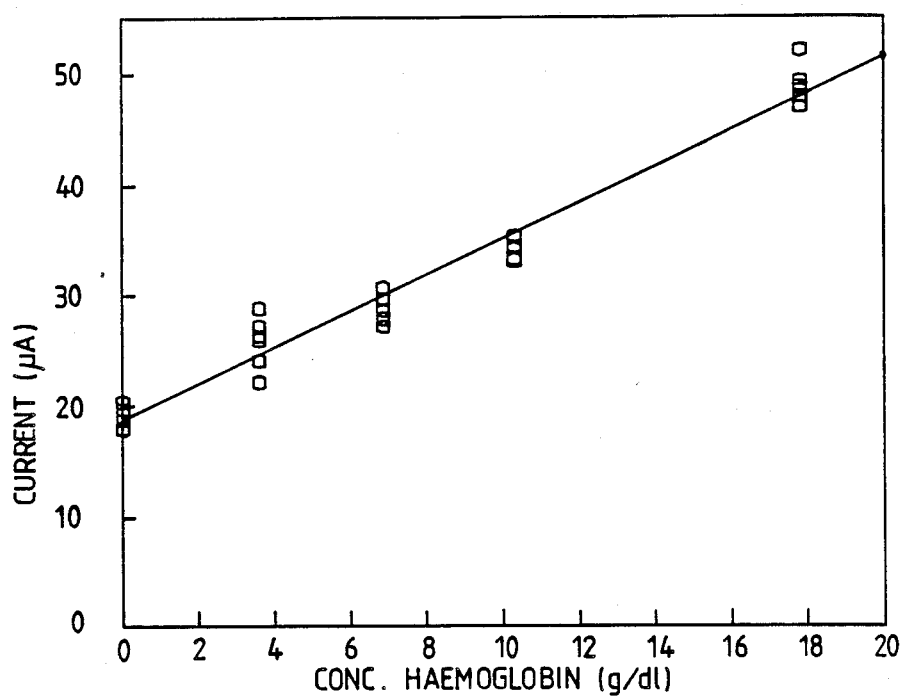

A sample volume of 20 μl whole blood was pipetted to cover both the working electrode of the mixture described above and an Ag/AgCl reference electrode adjacent but not contiguous and also located in electrical communication with separate conductive tracking, on a dry strip and incubated for 60 seconds to allow the ferricyanide to dissolve into the sample and oxidise the haemoglobin. Current-time transients were then recorded at +500 mV versus Ag/AgCl reference electrode and the current measured after 30 seconds. By using whole blood and whole blood diluted in serum, the calibration curves of FIG. 2 and 3 were constructed, comparing current responses with samples of known haemoglobin concentration as measured using a standard colorimetric technique (Drabkin's Reagent—Sigma Diagnostics).

More consistent results with better reproducability were obtained if the blood sample was lysed before contact with the working electrode.

EXAMPLE 5

Further experiments on the dry strip assay (i) In further experiments, a typical working electrode mix contained the following components:

10 g precipitated potassium ferricyanide
0.5 g silica HP240
1 g KCl

The mix was printed in both aqueous and organic (2-butoxyethanol) solvents. The organic solvent printed better to give more consistent results. The potassium ferricyanide was precipitated from aqueous solution with acetone and dried. Fine particles of potassium ferricyanide prepared by this method gave better data than ball-milled potassium ferricyanide.

(ii) The effects of pH on response were tested by including sodium bicarbonate in the working electrode mix and by varying the pH of a solution of haemolytic agent to which blood was added and incubated before application to the dry strip sensors. Variation of the pH over the range 6.1 to 8.1 produced not net change in the current response.

(iii) The calibration protocol was improved in order to obtain good calibration curves.

In one improved protocol, whole blood samples were diluted in serum from the same sample. To each was added a one-half (v/v) volume of a haemolysing agent comprising excess saponin in distilled water. 15 μl aliquots were added to the strips followed by a 30 second incubation before recording i-t transients at +450 mV versus Ag/AgCl.

In another improved protocol, whole blood samples were treated with a mixture of ferricyanide and saponin, as outlined previously, before application to a blank dry strip comprising the electrodes without the mix printed on the working electrode, and the i-t transients were measured at +450 mV versus Ag/AgCl.

In general, the on-strip calibration time could be from 5 seconds to 15 minutes, with the better results coming from the longer incubations.

Figure 4:
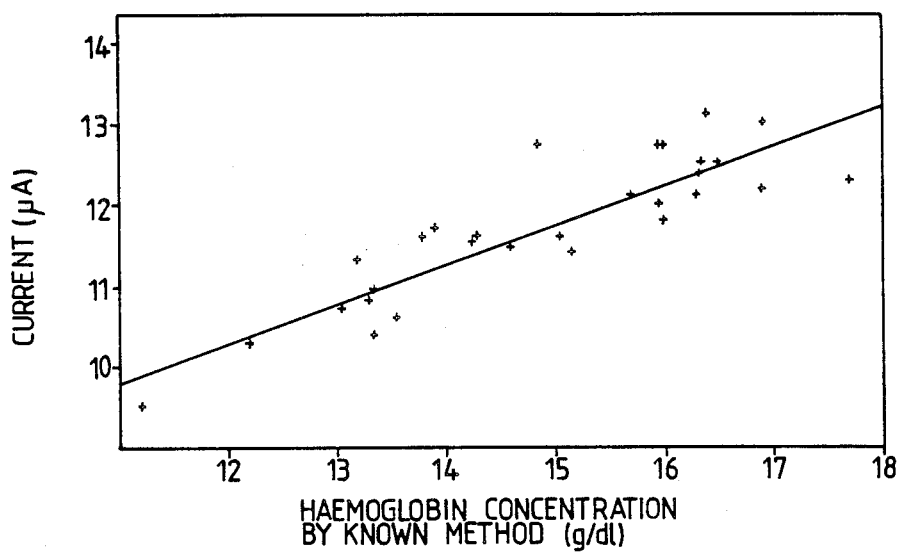
FIG. 4 is a calibration curve obtained in Example 5(iv), the measurements being on haemoglobin in g/dl as measured by a standard colorimetric technique.

(iv) A correlation with the Hemocue assay was performed, with the electrochemical assay of this invention using 50 μl blood and 50 μl of a mix of 30 mg/ml ferricyanide, 10 mg/ml saponin and 0.33% Triton X-100 (a Trade Mark for a polyoxyethylene ether), and 1 minute incubation before application of 15 μl to a dry strip sensor and recording the i-t transients at +450 mV versus Ag/AgCl, giving the results of FIG. 4.

Figure 5:
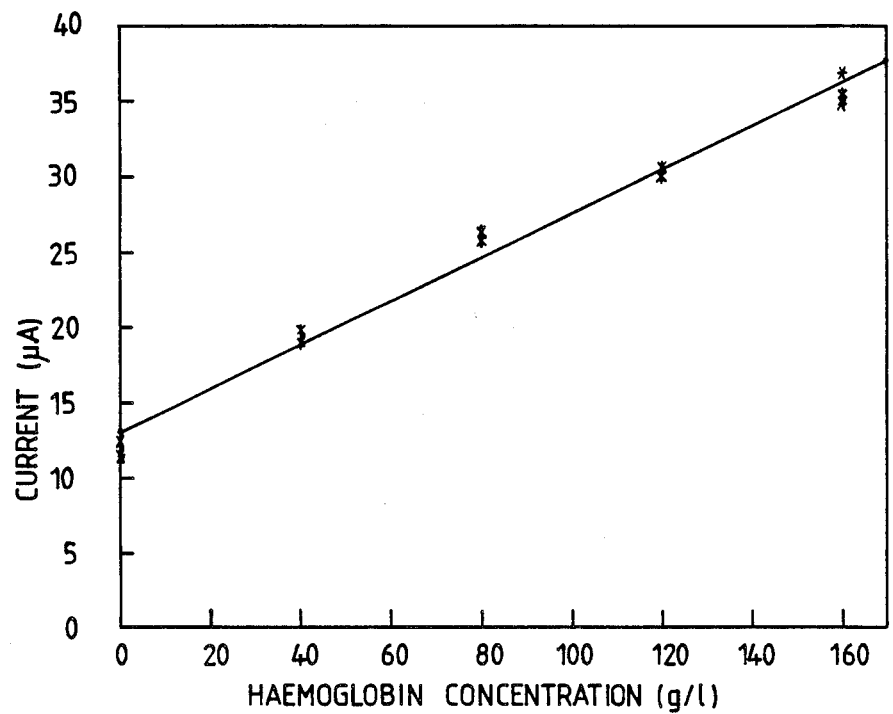
FIG. 5 is a calibration curve obtained in Example 5(v) with saponin in a mesh layer, showing current in microamps against haemoglobin content in g/dl.

(v) In a further variation, the lysing agent can be coated on a mesh laid over the working electrode. Such a system gave the results of FIG. 5.

Apart from saponin, other haemolytic agents include sodium deoxycholate, ionic detergents, and non-ionic detergents.

We claim:

1. A method for the assay of haemoglobin in blood comprising contacting the blood with a sufficient amount of a ferricyanide so that haemoglobin in the blood is reacted therewith and the haemoglobin is electrochemically assayed by monitoring the current change produced on reduction of the ferricyanide by the hemoglobin.

2. An assay method according to claim 1, wherein the blood is a sample of whole blood or a blood haemolysate sample.

3. An assay method according to claim 1, wherein the blood is provided as an unlysed sample, and the blood is treated with a haemolytic agent.

4. An assay method according to claim 1, wherein the current changes are monitored at a poised potential against a reference electrode.

5. An assay method according to claim 1, wherein the assay is performed using a dry strip sensor containing at least the ferricyanide.

6. An assay method according to claim 5, wherein the dry strip sensor is screen printed with a dry mixture containing finely divided ferricyanide, a surfactant, 7. An assay method according to claim 6 wherein said dry mixture further comprises a buffering agent.

8. An assay method according to claim 1, where said amount of ferricyanide is between 50 and 100 mg per ml of whole blood.

* * * * *